United States Patent [19]

Kovach

[11] Patent Number: 4,946,377

[45] Date of Patent: Aug. 7, 1990

[54] TISSUE REPAIR DEVICE

[75] Inventor: Larry J. Kovach, Flagstaff, Ariz.

[73] Assignee: W. L. Gore & Associates, Inc., Newark, Del.

[21] Appl. No.: 432,096

[22] Filed: Nov. 6, 1989

[51] Int. Cl.$^5$ ............................................. A61F 2/08
[52] U.S. Cl. ....................................................... 623/13
[58] Field of Search ................... 623/13, 1, 11, 12, 66, 623/901

[56] References Cited

U.S. PATENT DOCUMENTS

| | | | |
|---|---|---|---|
| 3,973,277 | 8/1976 | Semple et al. | 623/13 |
| 4,149,277 | 4/1979 | Bokros | 623/13 |
| 4,731,084 | 3/1988 | Dunn et al. | 623/13 |
| 4,759,765 | 7/1988 | Van Kampen | 623/13 |
| 4,772,288 | 9/1988 | Borner et al. | 623/1 X |
| 4,790,850 | 12/1988 | Dunn et al. | 623/13 |
| 4,792,336 | 12/1988 | Hlavacek et al. | 623/13 |

FOREIGN PATENT DOCUMENTS

| | | | |
|---|---|---|---|
| 106501B1 | 4/1984 | European Pat. Off. | 623/13 |
| 241252A2 | 10/1987 | European Pat. Off. | 623/13 |
| 317408A1 | 5/1989 | European Pat. Off. | 623/13 |

OTHER PUBLICATIONS

Active Tendon Prosthesis: Technique and Clinical Experience (Chapter 38) publication by James M. Hunter, pp. 682-692.

Primary Examiner—Ronald L. Frinks

[57] ABSTRACT

A prosthetic tissue repair device having one or more eyelets, intended for use in the augmentation or replacement of biological tissue, and to a method of making such a device, and to a method of using such a device. The device is intended to function in parallel with or in place of biological tissue so that it is partially or entirely responsible for the forces normally transmitted through the tissue and can be intended to function in this capacity either temporarily, i.e., during healing of the biological tissue, or permanently, i.e., to replace the biological tissue.

16 Claims, 3 Drawing Sheets

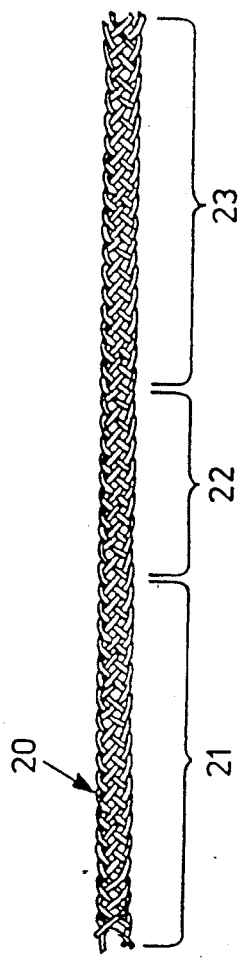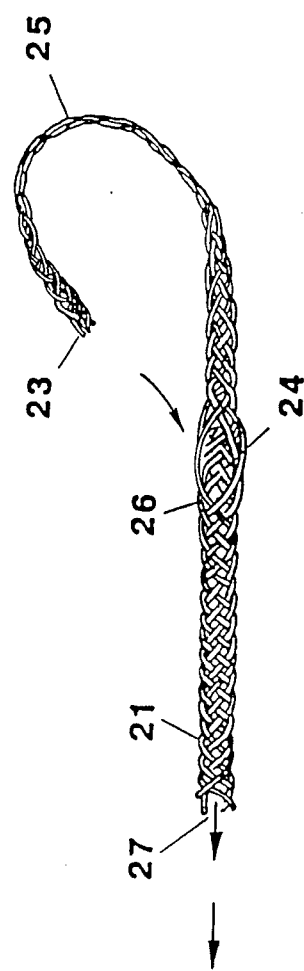

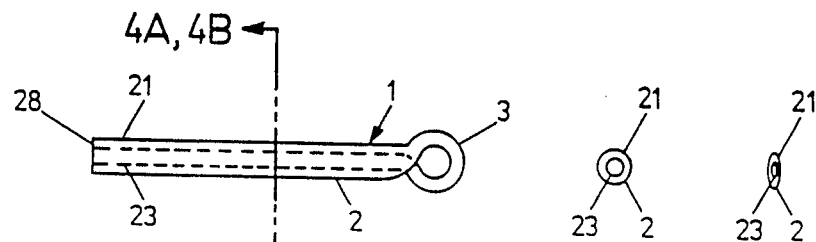
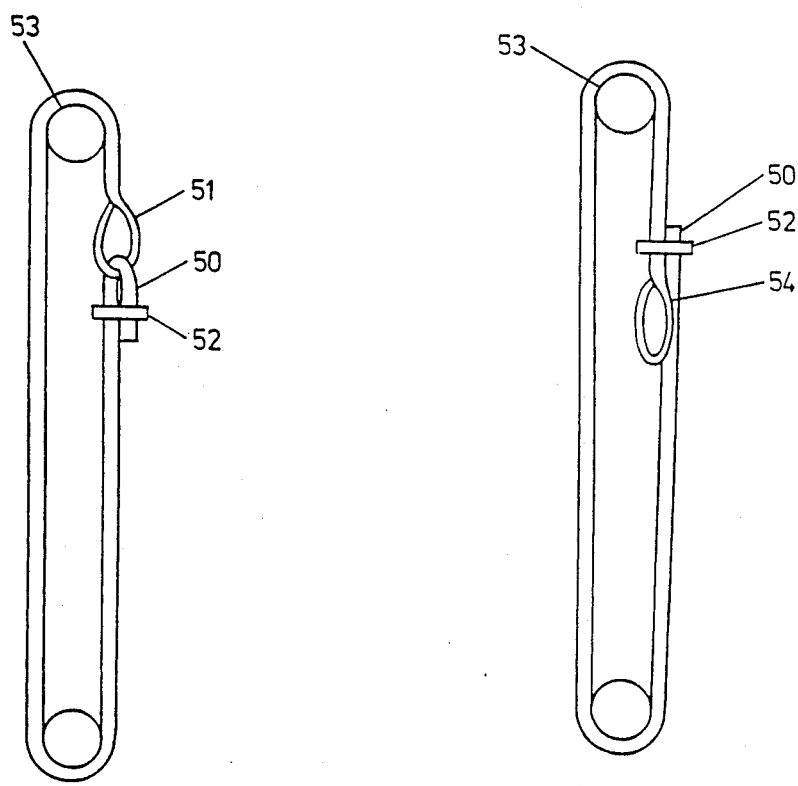
Fig. 4
Fig. 4A  Fig. 4B
Fig. 5
Fig. 6

TISSUE REPAIR DEVICE

FIELD OF THE INVENTION

This invention relates to a prosthetic tissue repair device having one or more eyelets, intended for use in the augmentation or replacement of biological tissue, and to a method for making such a device.

BACKGROUND OF THE INVENTION

Implantable tissue augmentation devices and tissue replacement devices have been used for many years for the augmentation or replacement of damaged biological tissue where this tissue provided the mechanical connection and support responsible for the forces involved in moving related anatomical structures, this tissue generally being in the form of ligaments and tendons. Tissue augmentation devices are used to augment the function of biological tissue, i.e. such devices will carry a portion of any imposed mechanical loads and will assist the biological tissue in carrying such loads, either temporarily, during healing of damaged biological tissue, or permanently. Tissue replacement devices carry the entire mechanical load and so replace the function of the biological tissue. Both tissue augmentation devices and tissue replacement devices are hereinafter collectively referred to as tissue repair devices.

There are many specific applications of tissue repair devices. For example, they are utilized for shoulder rotator cuff repair, acromioclavicular separations, and ligaments of the knee such as anterior cruciate and medial and lateral collateral. Additional examples include the repair of lateral collateral ligaments of the ankle and the repair of large tendons such as the achilles, quadriceps and patellar tendons, and small tendons such as flexor and extensor tendons of the hand.

Tissue repair devices for either replacement or augmentation are most typically manufactured of biocompatible polymers such as polytetrafluoroethylene (hereinafter PTFE), porous PTFE, polyester, polyamide, polypropylene or polyethylene terephthalate. They may also be made entirely or partly of biodegradable materials. The construction of tissue repair devices comprised at least partly of biodegradable materials is taught by U.S. Pat. Nos. 4,759,765; 4,772,288; and 4,792,336, and by European Patent Application No. 0241252A2. Such devices are typically of rope or cord-like form made of multiple strands that may be braided or woven together. They may incorporate an eyelet at one or both ends, the eyelet being intended to accept a bone screw for attaching the eyelet end of the device to an adjacent bone.

Single eyelet devices have also been used for cerclage applications in which the length of the single eyelet device encircles the member or members to which it is to be attached, the end of the device opposite the eyelet being inserted through the eyelet and pulled taut. The second end of the device is then attached back to the encircling part of the device or to a separate attachment point. Cerclage techniques have been used for the repair of, for example, incompetent uterus and for ileocecal bypass. The advantage of this type of repair is that the tissue repair device is only required to be attached by the surgeon at the end opposite the eyelet, thus saving operational time and expense.

The eyelets of previous tissue repair devices have often been formed by bending the length of material back on itself at its longitudinal midpoint so that the ends of the material are parallel and adjacent to each other. The two parallel ends are then secured together using additional material in any acceptable fashion, leaving an eyelet at the midpoint of the original length of material. Alternatively, in the case of devices having multiple strands braided together, eyelets are sometimes formed by weaving the ends of the strands back into the strands of the body of the device so that an eyelet is fashioned and no strand ends are left exposed at the eyelet end, this method being similar to that used to form an eye-splice in a rope end. Still another method of making an eyelet, described in European Patent Application No. 0106501A1 involves forming the material of the prosthetic into the desired shape under heat and pressure. Another method involves bonding or mechanically attaching a separate eyelet to the remainder of the tissue repair device. These methods are often difficult and time-consuming to manufacture. Many require the use of additional securing material such as sutures or adhesives. Most of them compromise the strength of the completed device so that failure is likely to occur at the point at which the eyelet attaches to the remainder of the device.

SUMMARY OF THE INVENTION

A tissue repair device comprised of a length of braided, biocompatible material having a hollow core for the entire length is described, said length having a first end portion, a second end portion disposed within the hollow core of the first end portion rendering the first and second end portions coaxial with each other, and a middle portion looped to form an eyelet. A method for producing this device is also described.

BRIEF DESCRIPTION OF THE DRAWINGS

FIG. 2 shows a length of multiply stranded braided biocompatible material prior to making the length into a tissue repair device. The two end portions and the middle portion that will become respectively the coaxial part and the integrally adjoined eyelet part of a completed tissue repair device are shown.

FIG. 2A shows a cross section of the length of braided, biocompatible material having a hollow core.

FIG. 3 shows a length of braided biocompatible material with the braid strands separated so as to form an opening into which the first end of the braided material is about to be inserted.

FIG. 4 shows a schematic drawing of a completed tissue repair device of the present invention having a coaxial part and one adjoining eyelet part.

FIG. 4A shows a schematic cross section of the coaxial part of the device shown in FIG. 4.

FIG. 4B shows a schematic cross section of the coaxial part of the device shown in FIG. 4, the coaxial part of the device having been flattened.

FIG. 5 shows a cerclage, the testing of which is described in Example 2.

FIG. 6 shows a cerclage, the testing of which is described in Example 2.

DETAILED DESCRIPTION OF THE INVENTION

Figure 1:
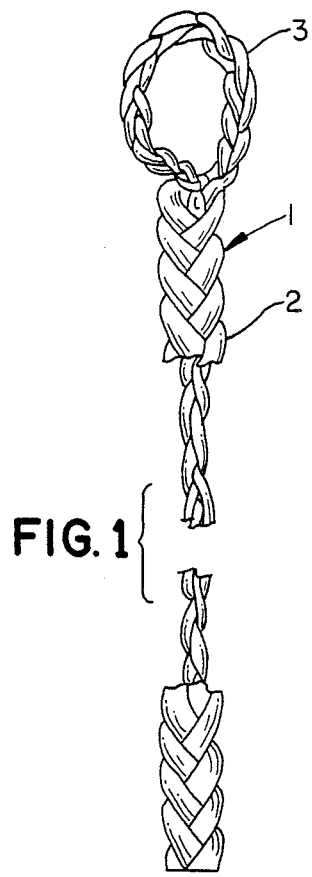
FIG. 1 shows a tissue repair device having one coaxial part and one adjoining eyelet part, made from a length of braided biocompatible material having a hollow core according to the method of this invention.

The present invention provides a tissue repair device of multiply stranded braided biocompatible material having one coaxial part integrally adjoined to at least one eyelet part. The single eyelet form of this device is so designed that the eyelet part and the point at which it integrally and continuously adjoins the coaxial part have tensile strength virtually equivalent to that of the coaxial part alone. A method of producing this device is also described, the method being simple and inexpensive in comparison to existing techniques for forming eyelets on tissue repair devices.

The braided biocompatible material of which the device is made is formed of a multiplicity of individual strands arranged so that the braided construction is of tubular form, possessing a hollow core centered along the longitudinal axis of the material and extending for the full length of the material. This multiply-stranded braided material having a hollow core may be of circular cross section, or of oblong cross section by flattening the hollow core.

The braided material may be any biocompatible material with adequate mechanical strength. Such materials include PTFE, porous PTFE, polyester, polyamide, polypropylene, and polyethylene terephthalate. Some or all of the strands may be comprised of biodegradable materials, e.g., polyglycolic acid (PGA), polylactic acid (PLA), PLA/PGA copolymer, polydioxanone (PDS) or certain polyesteramides if it is desired to have part or all of the device biodegrade over time as healing occurs and mechanical loads are again able to be carried by biological tissue. The optimum rate of degradation of the biodegradable strands will vary depending upon the particular tissue being repaired or reconstructed and will have to be determined empirically. Such use of biodegradable materials for implantation is well known to those skilled in the art of biomaterials.

FIG. 1 shows a tissue repair device (1) having a single eyelet (3) integrally and continuously adjoined to a coaxial part (2). FIG. 2 shows the starting material used in making the tissue repair device wherein the length (20) of multiply stranded braided biocompatible material is divided into three different portions (21,22,23). The first end portion (21) and second end portion (23) become the coaxial part (2) of FIG. 1 and the middle portion (22) becomes the eyelet (3) of FIG. 1. The second end portion (23) is designed to lie within the longitudinal hollow core of the first end portion (21) in a coaxial manner. The middle portion (22) of the original length (20) remains integrally and continuously adjoined to the first (21) and second (23) end portions.

FIG. 3 shows an initial step in the process of making a single eyelet tissue repair device. The eyelet part of the present invention is made by separating the individual strands of the braid so as to form an opening (24) in the hollow core braided material. The opening should be carefully enlarged until it is larger than the original diameter of the braided material. The individual strands should suffer no mechanical damage during the forming of this opening. The second end portion (23) of the braided material is turned back to the formed opening, thus curving this portion of the length of material into a loop (25). The second end portion (23) of the braided material is fed into the formed opening (24) and further fed through the longitudinal hollow core (26) of the first end portion (21) towards its tip (27), reducing the size of the loop (25) until it becomes an eyelet (3) of the desired size. During the process of forming the eyelet (3), it may be helpful to compress the length of the first end portion (21) of the material so as to increase the diameter of the longitudinal hollow core (26) and better enable the second end portion (23) of the material to be fed through. The completed single eyelet tissue repair device (1) is shown schematically in FIGS. 4 and 4A, wherein the second end portion (23) is seen to lie within and parallel to the hollow core of the first end portion (21) in a coaxial manner to form the coaxial part (2) of the single eyelet device (1).

The tip (28) of the coaxial part (2) should preferably be cut across the axis of the coaxial part to achieve the desired finished length and so that both of the original ends of the material are even with each other. The ends of the individual strands should preferably be bonded together. This may be accomplished by heating the tip (28) adequately to cause the strands to melt and adhere to each other, or by the application of an adhesive such as Dow Corning Silastic ® Silicone Medical Adhesive to the tip (28), or by mechanical means such as a metal tube crimped around the tip (28), or by any other suitable means. In this manner the individual strands comprising the tip of the device can be prevented from becoming separated.

An eyelet (3) formed in the manner described above, is simple to manufacture and causes no discontinuity in the strength of the completed device. The first and second end portions of the braided construction bind against each other when tension is applied to the device. As the load is increased, the outer first end portion of the braid tightens against the inner second end portion thus preventing the two portions of the braided material from slipping apart longitudinally. It is important the length of the coaxial part be adequate to prevent such slippage. This length will depend primarily on the ultimate applied tension, on the frictional characteristics of the material used, the density of the braid and the number and diameter of the individual strands. This limitation is less critical if the first and second end portions are physically secured to each other in a suitable manner, e.g., by suturing.

Variations on the technique described above for making a single eyelet device may be used to make tissue repair devices having eyelets at both ends. For a two eyelet device, two openings are formed by separating the strands of the braid at two different points along the length of braided material. The end segment adjacent to each opening is fed into that opening and into the hollow core of the braid toward the center of the length of material.

In additional embodiments of this invention, the eyelet formed according to the method of this invention may be further reinforced with heat, pressure, or with the use of an adhesive.

In still another embodiment, the finished tissue repair device may be of other than round cross section as shown by the schematic cross section of FIG. 4B. Such a device of oblong or flattened cross section may be made of a length of multiply stranded braided biocompatible material having a longitudinal hollow core wherein this material is of oblong or non-round cross section. Likewise, the complete finished tissue repair device or its coaxial part only may be flattened under heat, pressure or both.

EXAMPLE 1

PTFE dispersion powder ("Fluon CD 123" resin produced by ICI America) was blended with 130 cc of "ISOPAR K" odorless solvent (produced by Exxon Corporation) per pound (0.45 kg) of PTFE, compressed into a pellet, and extruded into a 0.274 cm diameter rod in a ram extruder having a 96:1 reduction ratio in a cross section by area.

The extruded rod still containing Isopar K was immersed in a container of Isopar K at 60° C. and stretched to 8.7 times its original length between capstans with an output velocity of about 26.3 m/min., forming a strand. These capstans were about 7.1 cm in diameter with a center-to-center distance between them of about 11.4 cm. The diameter of the strand was reduced from about 0.274 cm to about 0.119 cm by this stretching. The Isopar K was then removed from this stretched material by heating the material in an oven set at about 350° C. for a period of about 5 minutes.

The stretched strand was then pulled through a circular densification die heated to 300° C. The opening in the die tapered at a 10° angle from about 0.127 cm to about 0.064 cm and then was constant for about 0.064 cm length. The output velocity of the material exiting the die was 2.19 m/min.

The stretched strand was then heated to 300° C. through contact with heated driven capstans and stretched 350% with an output velocity of 1.98 m/min. These capstans had diameters of 7.1 cm and had a center-to-center distance between them of 11.4 cm.

Finally the strand was restrained from shrinking and exposed to about 367° C. in an air oven for 30 seconds.

In the finished form the strand made with this process possessed the following characteristics:
Diameter=0.066 cm
Porosity=80.8%
Porosity, as used here is defined as:

$$\text{Porosity} = \frac{[1 - p_2]}{p_1} 100\%$$

where:
$p_2$=density of porous material
$p_1$=of solid PTFE making up the solid content of the porous material, 2.2 g/cc for the solid PTFE described above.

Sixteen strands of the material described above were braided together on a sixteen bobbin New England Butt braiding machine running at 150 rpm. A braid of approximately 3.5 picks per centimeter was created, "pick" meaning the crossing of one strand over another, these crossings being counted along the longitudinal axis of the braid. The finished braided material had an outside diameter of about 2 mm with a hollow core.

A 25 cm sample of this braided material was cut from the total length manufactured for the purpose of fashioning a tissue repair device. A single eyelet tissue repair device was made from the 25 cm sample by separating the braid near the longitudinal center of the sample until an opening into the braid was created between the strands forming the braid. The opening was carefully enlarged, simultaneously enlarging the outside diameter of the braided material and the diameter of the hollow core. When the opening was about 5 mm wide, the first end of the sample was inserted into the opening and fed back through the longitudinal hollow core toward the second end of the sample until an eyelet of about 0.65 cm diameter remained. The end of the device opposite the eyelet was cut off square so that the overall finished length of the device was about 12 cm. Both the outer first end and inner second end were cut through simultaneously at this location.

This device was then tested in tension to failure on an Instron model 1122 tensile testing machine. A horizontally oriented cylindrical steel pin of 5 mm diameter was inserted into the eyelet of the tissue repair device. The pin was gripped within the upper grip of the Instron and the opposite end of the tissue repair device was gripped directly within the lower Instron grip so that the length under test was 10 cm. The crosshead speed was set to be 3.33 mm/second. The tissue repair device broke at a force of 65.5 kg at the Instron grip opposite the eyelet end.

For comparison, a second tissue repair device was made of the same braided hollow core material. This second device had no eyelets and consisted of only a coaxial part. It was made by cutting a 25 cm length of the material in half transversely and placing one half within and parallel to the longitudinal hollow core of the other half in a coaxial manner, the result being a 12.5 cm length of coaxial material without an eyelet at either end. This second device was tested in tension to failure in the same manner as the first, except that both ends of the second device were gripped within the Instron grips with a grip separation of 10 cm. This second device broke at a force of 64.5 kg at one of the Instron grips. The tissue repair device of the present invention, having an eyelet at one end, demonstrated virtually the same minimum tensile strength as an equivalent device not having an eyelet.

EXAMPLE 2

This example demonstrates the strength advantage of a single eyelet device of the present invention in a cerclage type of application.

Two single eyelet devices of 40 cm finished overall length were manufactured from a 3.5 picks/cm braided material comprised of 8 strands of the PTFE material previously described. Both finished devices were configured into loops, as shown in FIGS. 5 and 6. The cerclage of FIG. 5 was formed by inserting the end opposite the eyelet (50) through the eyelet (51), folding it back on itself and securing it with an electrical crimp connector (52). The cerclage of FIG. 6 was formed by securing the end opposite the eyelet (50) to the straight portion of the device adjacent to the eyelet (54), again using an electrical crimp connector (52) of the same type. Each cerclage was then tested in tension to failure by placing the cerclage over a 6.4 mm diameter steel pin (53) clamped within each grip of a model 1122 Instron tensile tester and applying tension t a rate of 200 mm per minute. Each pin (53) was perpendicular to the plane formed by the cerclage. Both devices failed by pulling apart at the electrical crimp connector (52). The device shown in FIG. 5 failed at 39 kg.; the eyelet formed by the method of the present invention remained intact. The device shown in FIG. 6 failed at 11 kg.

The electrical crimp simulated an attachment that would be required of a surgeon implanting a tissue repair device with a cerclage technique. The single eyelet device of the present invention, offering an eyelet of strength virtually equivalent to the straight portion, allows reduced loading of the surgeon's attachment when the eyelet is used to form the cerclage. This technique allows a surgeon to take advantage of the mechanical strength of the single eyelet tissue repair device of the present invention.

I claim:

1. A tissue repair device comprised of a length of braided, biocompatible material having a hollow core for the entire length, said length having a first end portion, a second end portion disposed within the hollow core of the first end portion rendering the first and second end portions coaxial with each other, and a middle portion looped to form an eyelet.

2. The device of claim 1 wherein the length of braided biocompatible material is comprised of porous PTFE.

3. The device of claim 1 wherein the length of braided biocompatible material is comprised of polypropylene.

4. The device of claim 1 wherein the length of braided biocompatible material is comprised of polyester.

5. The device of claim 1 wherein the length of braided biocompatible material is comprised of polyethylene terephthalate.

6. The device of claim 1 wherein the length of braided biocompatible material is comprised of polyamide.

7. The device of claim 1 wherein at least part of the braided biocompatible material is comprised of a biodegradable material.

8. The device of claim 1 wherein at least part of the length of braided biocompatible material of tubular form is flattened.

9. A method of forming an eyelet at one end of a length of multiply-stranded braided biocompatible material for use as a tissue repair device, wherein said length has a first and second end and a hollow core connecting said ends, comprising the steps of:

(a) separating the strands of said braided material to form an opening into the hollow core of said braided material;

(b) inserting the first end of said braided material through the formed opening and into the hollow core of said braided material;

(c) feeding the first end of said braided material through the formed opening and the hollow core toward the second end of said braided material until the eyelet so formed is of the desired size.

10. The method of claim 9 wherein the length of multiply stranded braided biocompatible material is comprised of porous PTFE.

11. The method of claim 9 wherein the length of multiply stranded braided biocompatible material is comprised of polypropylene.

12. The method of claim 9 wherein the length of multiply stranded braided biocompatible material is comprised of polyester.

13. The method of claim 9 wherein the length of multiply stranded braided biocompatible material is comprised of polyethylene terephthalate.

14. The method of claim 9 wherein the length of multiply stranded braided biocompatible material is comprised of polyamide.

15. The method of claim 9 wherein at least some of the strands of the length of multiply stranded braided biocompatible material are comprised of a biodegradable material.

16. The method of claim 9 wherein the length of multiply stranded braided biocompatible material of tubular form is flattened.

* * * * *